United States Patent [19]

Howe et al.

[11] 4,208,510

[45] Jun. 17, 1980

[54] PREPARATION OF 3-ARYL-ISOXAZOL-5-YL BENZOATES

[75] Inventors: Robert K. Howe, Bridgeton; Kou-Chang Liu, Creve Coeur, both of Mo.

[73] Assignee: Monsanto Company, St. Louis, Mo.

[21] Appl. No.: 971,158

[22] Filed: Dec. 20, 1978

[51] Int. Cl.² .......................................... C07D 261/08
[52] U.S. Cl. .................................................. 548/247
[58] Field of Search ................................... 260/307 H

[56] References Cited

U.S. PATENT DOCUMENTS

| | | | |
|---|---|---|---|
| 3,947,263 | 4/1976 | Brouwer et al. | 260/307 G |
| 3,964,896 | 6/1976 | Brouwer et al. | 71/92 |
| 4,032,644 | 6/1977 | Nadelson | 260/307 H |

FOREIGN PATENT DOCUMENTS 1494877  12/1977  United Kingdom ................ 260/307 H

OTHER PUBLICATIONS

Wagner et al., "Synthetic Organic Chemistry," J. Wiley & Sons Inc., New York, (1953) pp. 495–496.

*Primary Examiner*—Anton H. Sutto
*Attorney, Agent, or Firm*—Patricia A. Coburn; Donald W. Peterson

[57] ABSTRACT

3-Aryl-isoxazol-5-yl benzoates are prepared by an acid catalyzed solvolysis of 3'-(Aryl)-spiro[isobenzofuran-1(3H),5'(4'H)-isoxazol]-3-one.

9 Claims, No Drawings

PREPARATION OF 3-ARYL-ISOXAZOL-5-YL BENZOATES

This invention relates to the preparation of isoxazol-5-yl benzoates that are useful in agriculture. Specifically, the isoxazol-5-yl benzoates prepared in accordance with the present invention have the following structure:

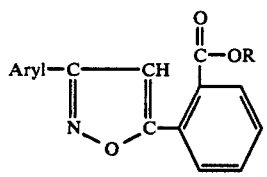

wherein R is hydrogen or R'CH$_2$— and R' is hydrogen or alkyl having up to four carbon atoms, inclusive.

Belgian Pat. No. 837,454 discloses such compounds to be effective plant growth regulants. In addition, U.S. patent application Ser. No. 796,248, filed May 12, 1977, now abandoned, U.S. patent application Ser. No. 907,069, filed May 18, 1978 and U.S. patent application Ser. No. 966,403, filed Dec. 4, 1978, all of which are herewith incorporated by reference, disclose that such compounds are useful in regulating the growth of desirable plants as well as controlling the growth of undesirable plants. Said applications disclose that the isoxazol-5-yl benzoates are prepared by conversion of isoxazolin-5-yl benzoate with N-bromosuccinimide or dichlorodicyanobenzoquinone. Isoxazolin-5-yl benzoates are prepared, however, from vinyl benzoates which are somewhat difficult to prepare.

In accordance with the novel aspects of the present invention, 3-Aryl-isoxazol-5-yl benzoates are prepared by an acid catalyzed solvolysis of 3'-(Aryl)-spiro[isobenzofuran-1(3H),5'(4'H)-isoxazol]-3-one. 3-(Aryl)-spiro[isobenzofuran-1-(3H),5'(4'H)-isoxazol]-3-ones have been disclosed in our co-pending application Ser. No. 971,462, filed simultaneously herewith (titled "3'-(Substituted Phenyl)-Spiro[isobenzofuran-1(3H),5'(4'H)-Isoxazol]-3-Ones and Their Use As Herbicides and Plant Growth Regulants"), which is herewith incorporated by reference, and are prepared as disclosed therein by reaction of a nitrile oxide with 3-methylenephthalide in accordance with the following equation:

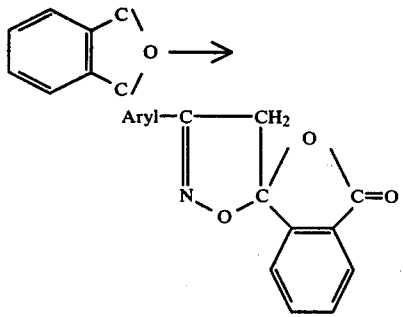

Since the Aryl radical takes no appreciable part in the reaction, any aromatic radical or heteroaromatic radical, e.g., pyridyl, may be used. Preferably, however, Aryl is a radical of the following formula

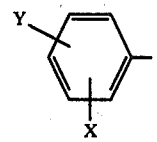

wherein X and Y are independently selected from the group consisting of hydrogen, halogen, lower alkyl, lower alkoxy, halo-lower-alkyl, phenoxy, and phenyl.

As used herein, the terms "lower alkyl" and "lower alkoxy" are understood to include those alkyl and alkoxy groups having up to five carbon atoms, inclusive. Both straight as well as branched chain alkyl groups are contemplated.

The term "halo-lower-alkyl" as used herein is understood to mean those lower alkyl groups in which at least one, and perhaps all, of the hydrogen atoms have been replaced by halogen atoms. It is to be clearly understood that trifluoromethyl is contemplated as being a halo-lower-alkyl moiety.

The term "halogen" as used herein includes chlorine, bromine, fluorine and iodine.

In accordance with the process of the invention, the spiro compound is reacted with a hydroxy compound in the presence of a catalytic amount of a strong acid as follows:

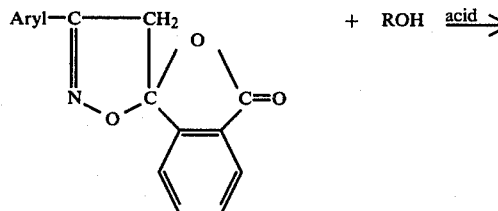

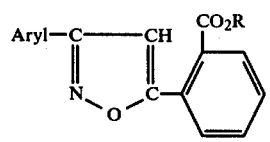

wherein R is hydrogen or R'CH$_2$— and R' is hydrogen or alkyl having up to four carbon atoms, inclusive. Said alkyl group may be a straight or a branched chain.

The specific acid used is not critical. However, the use of stronger acids increases the rate of reaction. Accordingly, strong acids such as hydrochloric acid, sulfuric acid, methanesulfonic acid, toluenesulfonic acid and the like are preferred.

Although the reaction may be conducted at room temperature, it is preferred to conduct it at or near the reflux temperature of the hydroxy compound.

The reaction may be conducted above atmospheric pressure. However, atmospheric pressure is preferred.

It should be noted that the invention contemplates the preparation of 3-Aryl-isoxazol-5-yl benzoic acid in addition to esters thereof. The free acid may be prepared in one of two ways. First, the spiro compound may be cleaved utilizing aqueous acid without any alcohol being present. In other words, the above reaction is utilized in which R is hydrogen. The free acid is also prepared by reaction of the spiro compound with an alcohol at low temperatures. At low temperatures and- /or short residence times, the preparation of free acid is favored. Thus, a mixture containing both the free acid and the ester may be formed. The amount of ester prepared in accordance with the novel process is dependent upon the temperature of the reaction and the length of time that the reaction is allowed to proceed. To prepare the ester, it is preferable to conduct the reaction at or near the reflux temperature of the hydroxy compound for a sufficient period of time in which to convert the spiro compound to the ester. Under such conditions, only minor amounts of the free acid are produced. If lower temperatures are utilized, a greater amount of the free acid would be produced. When preparing esters, it is preferable to use an excess amount of the hydroxy compound.

Generally, it has been found that the spiro compound is soluble in the hydroxy compound. If the spiro compound is not readily soluble in said hydroxy compound, it may be beneficial to utilize an inert solvent.

In order to illustrate the novel aspects of the present invention, the following examples are presented. Said examples are presented for illustration and are not intended as a limitation with respect to the scope of the invention.

EXAMPLE 1

Preparation of Methyl 2-(3-Pentafluorophenyl-5-Isoxazolyl)Benzoate

A solution of 3'-(pentafluorophenyl)-spiro[isobenzofuran-1(3H),5'(4'H)-isoxazol]-3-one (3.9 g., 0.0106 mole), concentrated $H_2SO_4$ (0.3 ml.) and methanol (100 ml.) was held at reflux for 30 hours, cooled and poured into 600 ml. of ice water. The mixture was extracted with 1 liter of ether. The organic extract was then washed two times with water, dried over $CaSO_4$ and concentrated under vacuum to 3.8 g. of crystals; m.p. 96.5°–98° C. Recrystallization of the crude ester from toluene-hexane gave 2.96 g. of pure product as colorless crystals; m.p. 97°–98° C.

Anal. Calc'd. for $C_{17}H_{18}F_5NO_3$: C, 55.30; H, 2.18. Found: C, 55.27; H, 2.21.

EXAMPLE 2

Preparation of Methyl 2-[3-(p-Trifluoromethylphenyl)-5-Isoxazolyl]Benzoate

Methyl 2-[3-(p-trifluoromethylphenyl)-5-isoxazolyl]benzoate was prepared according to the procedure of Example 1 in 82% yield as a colorless oil. The oil was crystallized from toluene-hexane to give 2.7 g. of white crystals; m.p. 90.5°–92° C.

Anal. Calc'd. for $C_{18}H_{12}F_3NO_3$: C, 62.25; H, 3.48. Found: C, 62.28; H, 3.51.

EXAMPLE 3

Preparation of Methyl 2-[3-(o-Methylphenyl)-5-Isoxazolyl]Benzoate

Methyl 2-[3-(o-methylphenyl)-5-isoxazolyl]benzoate was prepared according to the procedure of Example 1 as a colorless oil in 95% yield. The oil (3.99 g.) was purified by column chromatography on silica gel with 50% toluene—50% ethyl acetate as the eluant. One fraction contained 2.49 g. of pure product, $n_D^{25.8} = 1.6017$.

Anal. Calc'd. for $C_{18}H_{15}NO_3$: C, 73.71; H, 5.15. Found: C, 73.52; H, 5.20.

EXAMPLE 4

Preparation of Methyl 2-[3-[3-(Trifluoromethyl)-Phenyl]-5-Isoxazolyl]Benzoate

A mixture of 2 g. (0.006 mole) of 3'-(m-trifluoromethylphenyl)-spiro[isobenzofuran-1(3H), 5'(4'H)-isoxazol]-3-one, 2 ml. of concentrated sulfuric acid and 50 ml. of methanol was heated at reflux for 17 hours. The solution was then poured into 100 g. of ice and extracted twice with 300 ml. of ether. The ether solutions were combined, washed twice with water saturated sodium chloride, and dried over $CaSO_4$. Removal of the solvent gave 2 g. of colorless viscous liquid, which was crystallized from hexane at 0° C. to give colorless crystals; m.p. 46°–48° C.

EXAMPLE 5

Preparation of Methyl 2-[3-(p-Chlorophenyl)-5-Isoxazolyl]Benzoate

A solution of 6.3 g. (0.020 mole) of 3'-(p-chlorophenyl)-spiro[isobenzofuran-1(3H),5'(4'H)-isoxazol]-3-one, 2 ml. of concentrated $H_2SO_4$ and 300 ml. of methanol was stirred at reflux for 20 hours. The cooled solution was poured into ice water (3 liters) and extracted with ether. The combined organic extracts were washed twice with water, dried over $CaSO_4$ and concentrated under vacuum to yield 5.8 g. of colorless crystals (88%) of product. Recrystallization from hexane afforded 5.4 g. of an analytically pure sample; m.p. 89.5°–91° C.

Anal. Calc'd. for $C_{17}H_{12}NClO_3$: C, 65.14; H, 3.86. Found: C, 65.14; H, 3.90.

EXAMPLE 6

Preparation of Methyl 2-[3-(2,4-Dichlorophenyl)-5-Isoxazolyl]Benzoate

Methyl 2-[3-(2,4-dichlorophenyl)-5-isoxazolyl]benzoate was prepared in 94% yield with the same procedure as Example 5. Recrystallization of 4.7 g. of the crude product once from hexane and once from heptane yielded 3.3 g. pure crystals of the benzoate; m.p. 94°–96° C.

Anal. Calc'd. for $C_{17}H_{11}NCl_2O_3$: C, 58.64; H, 3.18. Found: C, 58.66; H, 3.19.

EXAMPLE 7

Preparation of Ethyl 2-[3-(2,4-Dichlorophenyl)-5-Isoxazolyl]Benzoate

A solution of 4 g. (0.011 mole) of 3'-(2,4-dichlorophenyl)-spiro[isobenzofuran-1(3H),5'(4'H)-isoxazol]-3-one, 2 ml. of concentrated $H_2SO_4$ and 200 ml. of ethanol was held at reflux for 19 hours, cooled, and poured into ice water. The resultant mixture was extracted twice with ether. The ethereal solution was washed twice with water, dried over $CaSO_4$ and concentrated under vacuum to give an oil. The oil was dissolved in hot hexane to afford 4.2 g. of a crystalline solid (96.9%). Recrystallization of the solid from hexane gave 3.1 g. of pure product; m.p. 85°–86° C.

Anal. Calc'd. for $C_{18}H_{13}NCl_2O_3$: C, 59.69; H, 3.62. Found: C, 59.66; H, 3.64.

EXAMPLE 8

Preparation of Methyl 2-[3-(3-Phenoxyphenyl)-5-Isoxazolyl]Benzoate

Methyl 2-[3-(3-phenoxyphenyl)-5-isoxazolyl]benzoate was prepared in accordance with Example 5 in 95% yield as a light brown oil. Chromatography on silica gel with 50% cyclohexane - 5% ethyl acetate as the eluant afforded pure product as a colorless oil; ir (CHCl$_3$) 1722 cm$^{-1}$; n$_D^{26.8}$=1.6217.

Anal. Calc'd. for C$_{23}$H$_{17}$NO$_4$: C, 74.38; H, 4.61. Found: C, 74.20; H, 4.68.

EXAMPLE 9

Preparation of n-Butyl 2-[3-(3-Trifluoromethylphenyl)-5-Isoxazolyl]Benzoate n-Butyl 2-[3-(3-trifluoromethylphenyl)-5-isoxazolyl]benzoate was prepared according to the procedure of Example 5 (utilizing n-butanol in lieu of methanol) in 94.8% yield as a pale yellow oil. The oil (5.54 g.) was dissolved in 25 ml. of hexane and cooled in dry ice to obtain a white solid at low temperature. This solid melted at room temperature and was chromatographed on a silica gel column with ethyl acetate as the eluant. 3.8 g. of pure product was obtained as a colorless oil; ir (CHCl$_3$) 1720 cm$^{-1}$; n$_D^{26.6}$=1.5412.

Anal. Calc'd. for C$_{21}$H$_{18}$F$_3$NO$_3$: C, 64.78; H, 4.66. Found: C, 64.78; H, 4.66.

EXAMPLE 10

Preparation of n-Pentyl 2-[3-(3-Trifluoromethylphenyl)-5-Isoxazolyl]Benzoate A solution of 3'-(m-trifluoromethylphenyl)-spiro[isobenzofuran-1(3H),5'(4'H)-isoxazol]-3-one (10 g., 0.03 mole) and concentrated H$_2$SO$_4$ (1 ml.) in n-pentyl alcohol (150 ml.) was held at reflux for 14 hours, cooled and poured into 300 ml. of ice water. The mixture was extracted with 600 ml. of ether. The ethereal solution was washed two times with water, dried over CaSO$_4$ and concentrated under vacuum to give 12.05 g. of product as a yellow oil (99%). The oil was chromatographed on silica gel using ethyl acetate as the eluant. 8.4 g. of colorless oil was collected; ir (CHCl$_3$) 1725 cm$^{-1}$; n$_D^{25}$=1.537.

Anal. Calc'd. for C$_{22}$H$_{20}$NF$_3$O$_3$: C, 65.50; H, 5.00. Found: C, 65.53; H, 5.06.

EXAMPLE 11

Preparation of Ethyl 2-[3-(3-Trifluoromethylphenyl)-5-Isoxazolyl]Benzoate

Ethyl 2-[3-(3-trifluoromethylphenyl)-5-isoxazolyl]benzoate was obtained in 97.7% yield as a viscous oil by the method described in Example 10 (ethanol used in lieu of n-pentyl alcohol). Crystallization of 5.3 g. of the oil from heptane-toluene yielded 3.7 g. of colorless crystals; m.p. 28°-30° C.

Anal. Calc'd. for C$_{19}$H$_{14}$F$_3$NO$_3$: C, 63.16; H, 3.91. Found: C, 63.13; H, 3.93.

EXAMPLE 12

Preparation of 2-[3-(3-Trifluoromethylphenyl)-5-Isoxazolyl]Benzoic Acid

A mixture of 0.28 g. of 3'-(3-trifluoromethylphenyl)-spiro[isobenzofuran-1(3H), 5'(4'H)-isoxazol]-3-one, 0.5 ml. of concentrated HCl, 10 ml. of water and 6 ml. of dioxane was stirred at reflux for one hour. The mixture was cooled and filtered to give 0.25 g. of white solid; m.p. 176.5°-178° C. in 89% yield.

EXAMPLE 13

Preparation of 2-[3-(2-Methylphenyl)-5-Isoxazolyl]-Benzoic Acid

A mixture of 0.26 g. of 3'-(2-methylphenyl)-spiro[isobenzofuran-1(3H),5'(4'H)-isoxazol]-3-one, 4ml. of water, 4 ml. of dioxane and 0.10 ml. of concentrated sulfuric acid was stirred at reflux for one hour, allowed to cool and diluted with 15 ml. of water. The resultant oil was stirred several minutes to give 0.24 g. of white solid; m.p. 162°-163.5° C. in 92% yield.

The above examples disclose, therefore, an efficient process for preparing isoxazol-5-yl benzoic acid and esters thereof that are useful as herbicides and plant growth regulants.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for preparing 3-Aryl-isoxazol-5-yl-benzoic acid and esters thereof having the formula

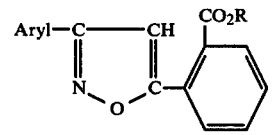

wherein R is hydrogen or R'CH$_2$— and R' is hydrogen or alkyl having up to four carbon atoms, inclusive which comprises reacting a spiro compound having the formula

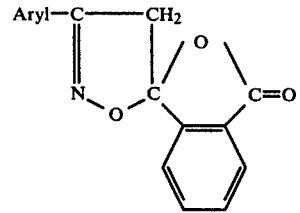

with ROH under acidic conditions at a temperature ranging from room temperature to the reflux temperature of the ROH compound.

2. A process according to claim 1 wherein said temperature is the reflux temperature of the ROH compound.

3. A process according to claim 1 wherein R is R'CH$_2$—.

4. A process according to claim 3 wherein an excess of said R'CH$_2$OH compound is utilized.

5. A process according to claim 1 wherein said Aryl is

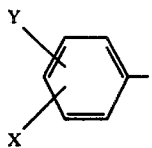

wherein X and Y are independently selected from the group consisting of hydrogen, halogen, lower alkyl, lower alkoxy, halo-lower-alkyl, phenoxy and phenyl.

6. A process according to claim 5 wherein X is hydrogen and Y is halo-lower-alkyl.

7. A process according to claim 6 wherein Y is trifluoromethyl.

8. A process according to claim 1 wherein said acidic conditions are obtained through the use of a catalytic amount of sulfuric acid.

9. A process according to claim 1 which comprises reacting a spiro compound of the formula

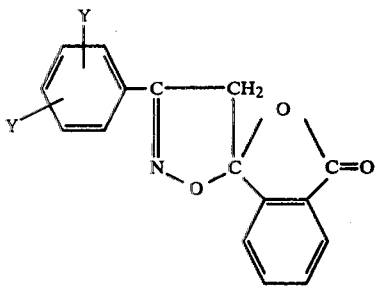

with R'CH$_2$OH in the presence of a catalytic amount of sulfuric acid.

* * * * *

UNITED STATES PATENT AND TRADEMARK OFFICE
CERTIFICATE OF CORRECTION

PATENT NO. : 4,208,510  
DATED : June 17, 1980  
INVENTOR(S) : Robert K. Howe et al.

Page 1 of 2

It is certified that error appears in the above—identified patent and that said Letters Patent is hereby corrected as shown below:

Column 1, first part of 2nd formula should read as follows:

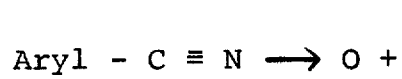 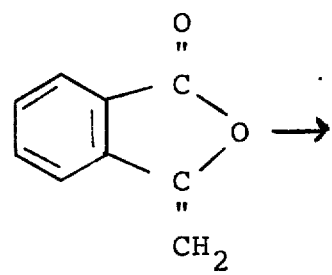

UNITED STATES PATENT AND TRADEMARK OFFICE
CERTIFICATE OF CORRECTION

PATENT NO. : 4,208,510
DATED : June 17, 1980
INVENTOR(S) : Robert K. Howe et al.

It is certified that error appears in the above—identified patent and that said Letters Patent is hereby corrected as shown below:

Column 8, Claim 9, the formula should read:

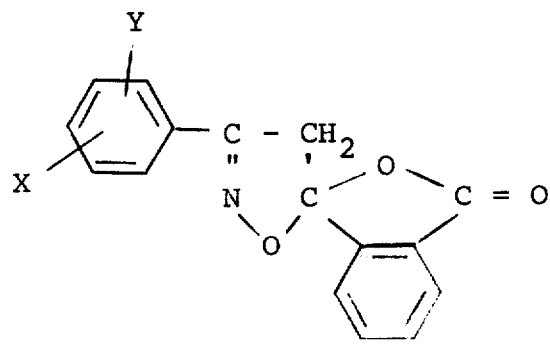

Signed and Sealed this

Ninth Day of December 1980

[SEAL]

Attest:

SIDNEY A. DIAMOND

Attesting Officer

Commissioner of Patents and Trademarks